United States Patent [19]

Wollenberg

[11] 4,388,471

[45] Jun. 14, 1983

[54] PROCESS FOR THE PREPARATION OF ALKENYL SUCCINIC ANHYDRIDES

[75] Inventor: Robert H. Wollenberg, San Rafael, Calif.

[73] Assignee: Chevron Research Company, San Francisco, Calif.

[21] Appl. No.: 373,471

[22] Filed: Apr. 30, 1982

[51] Int. Cl.³ .................... C07C 57/145; C07C 57/15; C07C 69/60; C07D 307/60
[52] U.S. Cl. .................................. 549/255; 560/190; 562/595
[58] Field of Search .................... 549/255; 560/190; 562/595

[56] References Cited

U.S. PATENT DOCUMENTS 3,412,111 11/1968 Irwin et al. .......................... 549/255
3,952,023 4/1976 Kaiya et al. ......................... 549/255

Primary Examiner—Richard Raymond
Attorney, Agent, or Firm—D. A. Newell; J. M. Whitney; J. J. DeYoung

[57] ABSTRACT

Disclosed is a process for the preparation of substituted carboxylic acids and their derivatives in which the synthesis reaction is carried out at least partially thermally in the presence of a furan-type compound. The furan-type compound substantially increases yields and reduces the formation of undesirable resinous by-products.

8 Claims, No Drawings

PROCESS FOR THE PREPARATION OF ALKENYL SUCCINIC ANHYDRIDES

FIELD OF THE INVENTION

This invention relates to an improved process for producing substituted carboxylic acids and their derivatives. More particularly, it relates to an improved process for the preparation of an alkenyl succinic anhydrides.

BACKGROUND OF THE INVENTION

The preparation of substituted carboxylic acids and their anhydrides and esters from such unsaturated acids or acid derivatives as maleic anhydride, fumaric acid or itaconic acid has been known for some time. The products are useful in many ways. For example, they serve as anti-rust agents in lubricants and fuels and as intermediates in the preparation of metal salts, esters and nitrogen-containing products which are useful as viscosity index improvers, dispersants and the like in lubricants and fuels. Other uses are also known to those skilled in the art. For example, alkenyl succinic anhydrides are used in paper sizing, paper pulp processing, wet strength agents, epoxy curing agents, and plasticizer esters for polyvinyl chloride.

The methods heretofore used for the preparation of the substituted carboxylic acids comprise alkylation of the unsaturated acid or acid derivatives with an aliphatic hydrocarbon or halogenated aliphatic hydrocarbon at a temperature above above 200° C. The earliest commercial processes generally utilized a thermal reaction wherein polyolefins of average molecular weight above about 200 were thermally reacted with maleic anhydride at temperatures in excess of 200° C. However, this thermal reaction suffers from a relatively low degree of conversion and if an attempt is made to improve the degree of conversion by increasing the temperature or pressure, an undesirable degradation of maleic anhydride occurs with resulting formation of carbon dioxide, water and tarry solids (resin). For this reason, resort has been made to initial preparation of a halogenated hydrocarbon reactant followed by reaction of the halogenated hydrocarbon with maleic anhydride (chlorination processes).

However, in these chlorination processes, a relatively high concentration of chlorine is in contact with the reaction vessel for substantial lengths of time, necessitating the use of special equipment for the entire reaction and the final product frequently contains undesirable residual chlorine. In attempts to overcome the problems associated with both the thermal and chlorination processes, researchers have devised various multistage processes and processes utilizing combinations of the thermal process and chlorination process. See for example, U.S. Pat. Nos. 3,231,587; 3,912,764; and 4,110,349.

SUMMARY OF THE INVENTION

It has been found that in a process for preparing a substituted carboxylic acid or derivative thereof from the thermal reaction of (A) a substantially aliphatic hydrocarbon containing an olefinic bond with (B) at least one of maleic acid, fumaric acid, itaconic acid and anhydrides and esters of these acids, that carrying out the reaction in the presence of a furan-type compound increases yields and reduces the formation of undesirable resinous by-products.

DETAILED DESCRIPTION OF THE INVENTION

As noted hereinabove, the chemicals used in the method of this invention are (A) a suitable alkylating hydrocarbon; (B) maleic, fumaric or itaconic acid or an anhydride or ester thereof; and a furan-type compound. If Reagent (B) is an ester, it is preferably a lower alkyl ester, the word "lower" denoting radicals having up to 7 carbon atoms. Most often, Reagent (B) is the free acid or the anhydride, and it is preferably maleic anhydride.

The alkylating hydrocarbon constituting Reagent (A) is a substantially aliphatic hydrocarbon which contains one olefinic bond but is otherwise substantially saturated. By "substantially aliphatic" is meant hydrocarbons containing no more than 10% non-aliphatic (i.e., aromatic or heterocyclic compounds). Suitable hydrocarbons include olefins, olefinic petroleum fractions, olefin polymers, oligomers, and copolymers. The invention will be described hereinafter principally with reference to olefin polymers which are preferred.

The olefin polymers are usually those prepared by polymerization of lower olefins, i.e., olefins, and olefin mixtures containing up to 7 carbon atoms. Suitable monoolefins include ethylene, propylene, 1-butene, 2-butene, isobutene and the pentenes, hexenes and heptenes (all isomers included).

The preferred olefin polymers are those derived from monoolefins, especially mono-1-olefins and more especially $C_{2-6}$ mono-1-olefins such as ethylene, propylene and the butenes. Homopolymers and interpolymers are suitable, and the interpolymers may be ordinary chain interpolymers or graft interpolymers. The preferred polymers are homopolymers and interpolymers derived from mixtures of monomers differing in size by at most about 2 carbon atoms, such as ethylene-propylene interpolymers and the polybutenes more fully described hereinafter.

As previously noted, the olefin polymer can contain minor proportions of alicyclic or aromatic carbon atoms which may be derived from such monomers as cyclopentene, cyclohexene, methylene cyclopentene, methylene cyclohexene, α-pinene, styrene and α-methylstyrene.

The olefin polymer usually contains about 30–300 and preferably about 50–250 carbon atoms. The number average molecular weight of the polymer, as determined by gel permeation chromatography, is ordinarily about 420–10,000, especially about 700–5,000 and more especially about 730–3,000.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as in the aforementioned U.S. Pat. No. 3,912,764. The above are incorporated by reference for their disclosures of suitable polybutenes and also for their description of suitable diluents as disclosed hereinafter.

In addition to the above-described alkylating hydrocarbons, many other alkylating hydrocarbons can be used. Other suitable alkylating hydrocarbons include cyclic, linear, branched and internal or alpha olefins with molecular weights in the range 42-1,000,000 or more with molecular weights in the range of 200-100,000 being more preferred. For example, alpha olefins obtained from the thermal cracking of paraffin wax. Generally, these olefins range from 5-20 carbon atoms in length. Another source of alpha olefins is the ethylene growth process which gives even number carbon olefins. Another source of olefins is by the dimerization of alpha olefins over an appropriate catalyst such as the well known Ziegler catalyst. Internal olefins are easily obtained by the isomerization of alpha olefins over a suitable catalyst such as silica.

As will be apparent from the above description, mixtures of alkylating hydrocarbons can be used as Reagent (A). Polymers, in fact, are inherent in such mixtures. It is also within the scope of the invention to use mixtures of polymers of different monomer combinations, such as a mixture of polybutene and polyethylene, a mixture of polybutene and an ethylene-propylene copolymer, or the like. Mixtures of acids, anhydrides and/or esters may also be used as Reagent (B); illustrative are maleic acid-fumaric acid mixtures, mixtures of methyl itaconate and methyl meleate, and mixtures of maleic acid and maleic anhydride. Most often, however, it is convenient and therefore desirable to use a single reagent as Reagent (B).

As used in the present invention, "furan-type compound" means a five-membered, oxygen-containing, heterocyclic-ring compound having two double bonds in the ring. Representative compounds include: furan, alkyl or dialkylfurans such as 3,4-dimethylfuran, 2,5-dimethylfuran, 2,3-dimethylfuran, 3-methylfuran, 3,4-diethylfuran, 3-t-butylfuran, etc. The alkyl group may contain 5 or more carbon atoms but preferably the alkyl group will contain 1-4 carbon atoms. Other furan-type compounds include furfural, furanoic acid, and benzofuran.

The molar ratio of Reagent (A) to Reagent (B) may vary according to the proportion of acid or acid derivative radicals desired in the product. Typically, about 0.2-2.0 moles of Reagent (B) are used per mole of Reagent (A), but it is usually desirable to use 0.5-1.5 moles and more preferably at least 1 mole of Reagent (B) per mole of Reagent (A) so as to minimize the amount of unreacted olefin polymer present in the product.

The reaction of Reagents (A) and (B) is carried out in the presence of an effective amount of the furan-type compound. By "an effective amount" is meant an amount sufficient to substantially reduce the formation of resinous by-products found in the typical prior art thermal process. Generally, these resinous by-products are believed to be found by the homopolymerization of the acid or acid derivatives [Reagent (B)]. Generally, this amount will range from 0.05-4.0 or more moles of furan-type compound per mole of Reagent (B), preferably 0.1-1 moles and more preferably 0.4-0.6 moles per mole of Reagent (B). It is believed that very small quantities of the furan-type compound may be effective in preventing resin formation. Although the formation of these resinous by-products is not completely understood, and with the understanding that Applicant does not wish to be bound by any particular theory, it is believed that the furan-type compound may undergo a reversible, cyclo addition, Diels-Alder-type reaction with the olefinic-bonded carbon atoms of the maleic anhydride thereby forming a thermally unstable compound which serves to substantially reduce the quantity of "free" maleic anhydride available for reaction at any particular time. Maintaining the quantity of "free" maleic as low as possible in the reaction mixture is believed to prevent the polymer formation.

The reaction can be carried out continuously or in a batch process and may be carried out in one or more stages, as is well known in the art. Furthermore, the process of this invention can be utilized in combination processes, e.g., the first step can be carried out as described herein and after separation of the furan-type compound, the second step may be carried out in the presence of chlorine. Preferably, the entire reaction is carried out thermally in the presence of the furan-type compound. The temperature employed may be in the range 50°-300° C., preferably 180°-285° C., and most preferably 200°-270° C. After the reaction, the furan-type compound can be stripped or separated from the reaction mixture by methods well known in the art.

The process will be further illustrated by the following representative examples.

EXAMPLES

EXAMPLE 1

Polybutenyl Succinic Anhydride Synthesis With Furan

Polybutenyl succinic anhydride (PIBSA) was prepared as follows: Approximately 1000 grams of polyisobutene (molecular weight 950) was mixed with 130 grams of maleic anhydride and 49 grams of furan. The resulting mixture was heated to 100° C. with stirring for 2 hours under an inert (nitrogen) atmosphere. The temperature was then raised to 245°-250° C. and held there for 8 hours. After cooling and thorough mixing of the reaction product, a 25-ml sample was removed for sediment (resin) analysis. The sample was diluted with 75 mls of light hydrocarbon and centrifuged at 6000 rpm for 15 minutes. The sample contained 0.45 weight percent sediment (resin). Chromatography of a portion of the PIBSA product showed that 75 weight percent of the polyisobutene had undergone conversion (saponification number 89). The infrared absorption curve showed a broad band at 1801 and 1877 cm$^{-1}$ indicating the presence of succinic anhydride.

EXAMPLE 2

Polybutenyl Succinic Anhydride Synthesis Without Furan

The same procedure and amounts described in Example 1 was followed except furan was omitted. The reaction was conducted initially at 100° C. and then at 245°-250° C. Analysis of a small sample indicated 5.3 weight percent sediment (resin) and 56 weight percent conversion of polyisobutene (saponification number 62). The infrared absorption curve was identical with that of the previous example.

Comparison of Examples 1 and 2 demonstrates the tremendous reduction in the quantity of resinous waste products, and the higher degree of conversion when carrying out the reaction in the presence of a furan-type compound.

It will be understood that various modifications of the invention can be practiced by those skilled in the art without departing from the scope and spirit of the invention.

What is claimed is:

1. In a method for preparing a substituted carboxylic acid or derivative thereof which comprises reacting (A) an alkylating hydrocarbon containing one double bond with (B) at least one of maleic acid, fumaric acid, itaconic acid and anhydrides and esters of any of these acids, at least part of the reaction being conducted thermally, the improvement which comprises conducting said thermal reaction in the presence of a furan-type compound.

2. The method according to claim 1 wherein said thermal reaction is carried out in the presence of an effective amount of said furan-type compound to substantially reduce the formation of resinous by-products.

3. A method according to claim 2 wherein Reagent (A) is an olefin polymer.

4. A method according to claim 3 wherein Reagent (B) is maleic anhydride.

5. A method according to claim 4 wherein said furan-type compound is selected from furan, 3,4-dimethylfuran, 2,5-dimethylfuran, or furfural.

6. A method according to claim 5 wherein said reaction is conducted in the presence of 0.05-4.0 moles of said furan-type compound per mole of Reagent (B).

7. A method according to claim 2 wherein Reagent (A) is a polyisobutylene polymer containing 30-300 carbon atoms, Reagent (B) is maleic anhydride, and said furan-type compound is furan which is present in said reaction in the range of 0.1-1.0 moles per mole of maleic anhydride.

8. A method of claim 7 wherein said reaction is carried out thermally at a temperature in the range 180°-275° C.

* * * * *